United States Patent [19]

Portmann et al.

[11] Patent Number: 5,792,426

[45] Date of Patent: *Aug. 11, 1998

[54] MULTI-WELL TITERPLATE FOR INSTRUMENTAL ANALYSIS

[75] Inventors: Rudolf Portmann, Bern; Andreas Hirschi, Interlaken; Andreas Wellenreiter, Wilderswil, all of Switzerland

[73] Assignee: Schweizerische Eidgenossenschaft Vertreten Durch Das AC-Laboratorium Spiez Der Gruppe Rustung, Spiez, Switzerland

[*] Notice: The term of this patent shall not extend beyond the expiration date of Pat. No. 5,540,891.

[21] Appl. No.: 668,937

[22] Filed: Jun. 24, 1996

Related U.S. Application Data

[63] Continuation-in-part of Ser. No. 321,395, Oct. 11, 1994, Pat. No. 5,540,891.

[51] Int. Cl.⁶ .................. B01L 3/00; B01L 9/00
[52] U.S. Cl. .................. 422/102; 422/99; 422/101; 422/104; 435/1; 435/305.2; 264/138; 206/443; 206/446; 211/74; 220/528; 220/533; 220/507; 220/527; 220/610; 220/611
[58] Field of Search .................. 422/99, 101, 102; 220/528, 529, 533, 527, 507, 611, 610; 206/443, 446; 211/74; 435/301; 356/244, 246; 264/138, 219, 333

[56] References Cited

U.S. PATENT DOCUMENTS

| | | | |
|---|---|---|---|
| Re. 34,133 | 11/1992 | Thorne | 422/99 |
| 3,649,464 | 3/1972 | Freeman | 220/507 |
| 4,154,795 | 5/1979 | Thorne | 422/99 |
| 4,385,115 | 5/1983 | de Zabala et al. | 435/33 |
| 4,526,690 | 7/1985 | Kiovsky et al. | 210/335 |
| 4,902,481 | 2/1990 | Clark et al. | 422/101 |
| 4,968,625 | 11/1990 | Smith et al. | 435/301 |
| 5,187,096 | 2/1993 | Glaever et al. | 435/291 |
| 5,265,754 | 11/1993 | Dalbo | 220/524 |
| 5,326,533 | 7/1994 | Lee et al. | 422/101 |
| 5,540,891 | 7/1996 | Portmann | 422/102 |

FOREIGN PATENT DOCUMENTS 2819820  11/1978  Germany.

*Primary Examiner*—Harold Y. Pyon
*Attorney, Agent, or Firm*—Schweitzer Cornman Gross & Bondell LLP

[57] ABSTRACT

A titerplate for instrumental analysis of liquid samples consists of a plurality of wells in which the walls and bottoms are made of two different materials with different physical properties. This allows the interfacial tension at the surface of the liquid to be controlled in such a way that it is essentially planar, allowing more accurate analysis to be performed on the samples. The bottoms of the wells are preferably made of a transparent material, so that the analysis and observation can be done in the transmission mode. The wells may be formed of radiation-absorbing material to prevent radiation cross talk between radioactive specimens. An overgarment replaceable film or foil having depressions aligned with the titerplate wells may be utilized to prevent contamination of the titerplate by samples and allow the reuse of the titerplate.

15 Claims, 5 Drawing Sheets

MULTI-WELL TITERPLATE FOR INSTRUMENTAL ANALYSIS

This is a Continuation-In-Part of U.S. patent application Ser. No. 08/321,395, filed Oct. 11, 1994, now U.S. Pat. No. 5,540,891.

The present invention relates to a titerplate of a multi-well configuration.

BACKGROUND OF THE INVENTION

Titerplates, and especially microtiterplates, are used more and more in the instrumental analysis of samples. Yet, it has been shown that the use of well known methods of photometric evaluation, such as the ELISA test (Enzyme Linked Immunosorbant Assay), the determination of enzyme activity, the evaluation of α and/or β radiation, the measurement of fluorescence or phosphorescence, etc., is often hampered, or the results falsified, by a meniscus which is formed on the surface of mostly aqueous samples subject to evaluation. The formation of a meniscus is the result of surface- and interfacial-tensions and, as a consequence of the wettability of the surfaces contacted by the liquid, the meniscus can be convex or concave.

Such improper results are also obtained using microtiter plates for the determination of radioactive samples, or RIA (Radio Immunesorbent Assay) by the photometric evaluation of radiation by liquid scintillation counting, where the main problem arises from the cross talk between neighboring sample wells containing different levels of radioactivity. Here the radiation is penetrating into adjacent wells and therefore appears as a higher activity than is actually present. This applies particularly with isotopes which give rise to high energy radiation, such as $p^{32}$. To avoid this problem, one calibrates the cross talk and corrects for it during the measurement. If the detector is located just above the well, then the influence of the geometry of the liquid surface shaped by the meniscus causes less deviation from the proper results; nevertheless, if one could correct for this as well, it would be of benefit. The third source for deviation from the proper results arises if the microtiter plates are molded from a transparent material, in which the walls can act as light conductor.

Furthermore, the evaluation of the toxicity of liquid solutions due to radioactive material by an alternative, semiautomatic assay, using small organisms like artemia which can be assayed in microtiter plates, is dependent on a proper image formed by trans-illumination. Only from an equally illuminated well with no surface deterioration can an analyzable image be obtained by a video camera and only such ideal pictures can be automatically analyzed for living or dead organisms. Thus, one is obliged to avoid meniscus formation as well as radiation passing from one well into the neighboring well to avoid improper results.

It is therefore the purpose of the present invention to create a multi-well structure for titerplates and the like which reduces to an acceptable level or prevents the formation of an interfering meniscus on the liquid surface, and/or prevents cross talk in liquid scintillation counting and in radio-toxicity assays, while not appreciably absorbing the instrumental analysis light ray, nor influencing the light path.

BRIEF DESCRIPTION OF THE INVENTION

In accordance with the present invention, materials having different physical properties are combined into an arrangement wherein the walls and the bottoms of the wells are joined in a manner in which the sample to be analyzed forms a boundary angle of about 90 degrees between the liquid and the wall. The bottoms of the wells are further configured to allow the rays used to pass therethrough without reflections, if appropriate, which can falsify the evaluation. In connection with the evaluation of radioactivity by liquid scintillation counting, as well as for measuring fluorescence and phosphorescence with the arrangement of the instrument's detector above the plate, the bottom of the wells is configured in such a way that light cannot pass therethrough, to avoid falsification of results.

In accordance with the invention, a variety of a multitude of suitable material combinations can be assembled.

The use of an apolar thermoplast for the well walls and a transparent thermoplast for the well bottoms provides a preferred construction for the observation of aqueous, and therefore polar, samples. Well bottoms can be formed as a matrix of elevations in a plate-like element. The well walls can be mounted thereon with a friction fit to minimize or avoid welding or gluing. Such a formation also allows an indexing system of coordinates to be used to locate and identify the samples.

In connection with liquid scintillation counting, slightly apolar/polar liquid systems are most often used, and therefore a polar thermoplast with the addition of radiation-absorbing materials is preferably used for the walls of the wells. This allows the formation of the desired planar surface of the liquid as well as preventing cross talk. The well bottoms may be either formed of a transparent or opaque thermoplast, depending from the arrangement (below or above the plate) of the detector in the instrumentation. A sheet or film-like cover or "overgarment" having formed indentations or cavities may be used in conjunction with the plate to prevent contamination of the plate and thus allow reuse thereof.

In a preferred embodiment, sub-assemblies having a plurality of well walls may be mounted upon a base plate and elevation unit to form a large-scale multi-element plate system. The assemblies may be provided with holes or apertures through which indexing spigot shafts extend to align and mount the sub-assemblies to a base plate element.

BRIEF DESCRIPTION OF THE DRAWINGS

In the following description the objects and features of the invention will be explained in more detail, and may be reviewed in conjunction with the annexed drawings, in which.

DETAILED DESCRIPTION OF THE INVENTION

Figure 1:
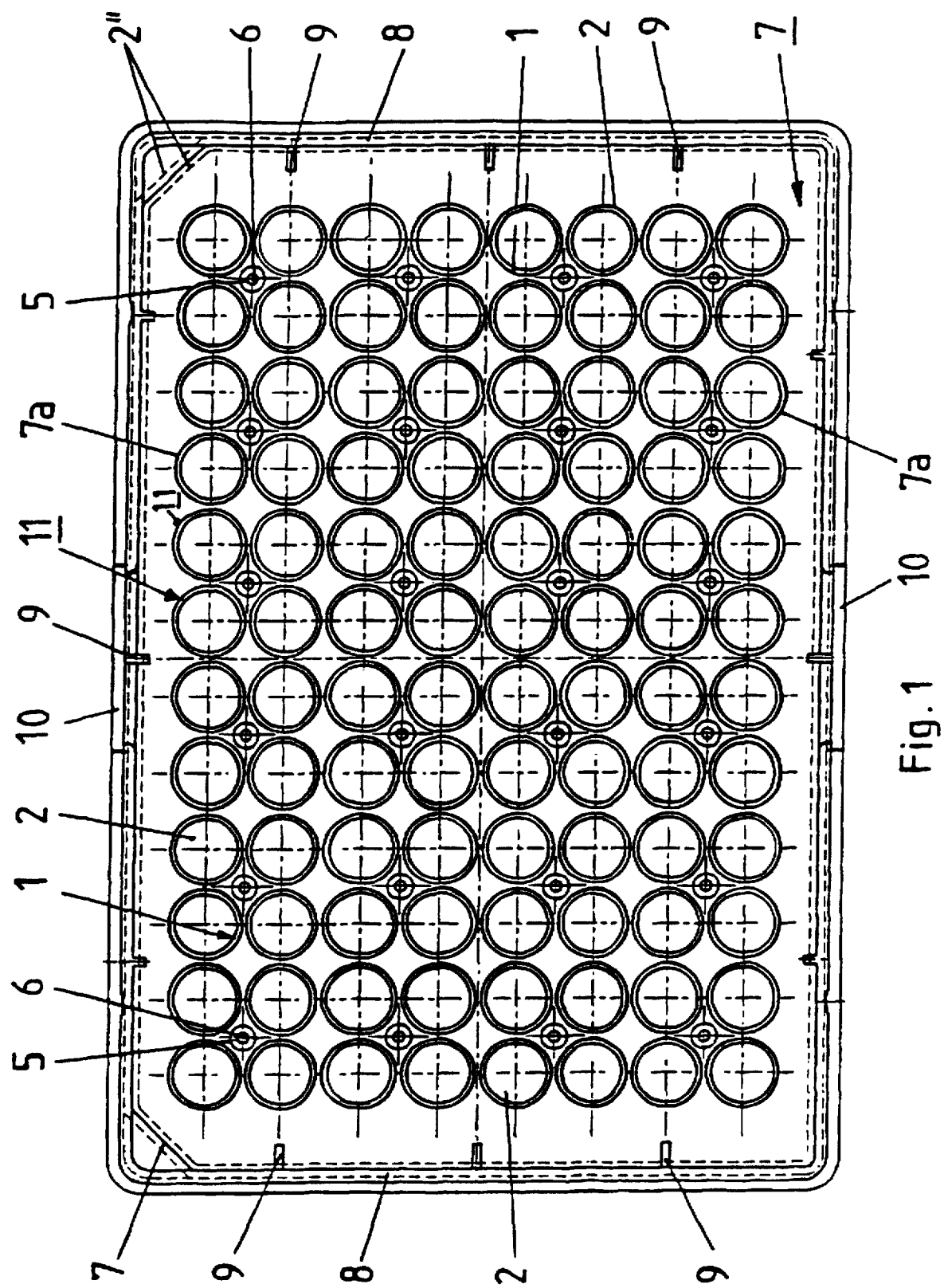
FIG. 1 depicts in a plan view a microtiter plate in accordance with the invention with a transparent protective cover.

Referring initially to FIG. 1, a multi-well titerplate assembly is shown having an array of 96 individual wells 11. Each well includes a well bottom 2 preferably formed as part of a plate or sheet-like bottom plate structure 2", and an upstanding cylindrical wall 1, which may be similarly formed as part of a multi-well forming element. The array of well bottoms lie in a common plane. A series of vertical distance-gauging elements or shafts 6 extend upwardly from the bottom plate 2", and are aligned with spigot holes 5 formed in the wall forming elements. An overlying frame cover 7 includes holes 7a for the upper ends of the well walls 1. The well bottoms are typically transparent, and, along with the walls, may be provided at least partially with a surface adapted to adsorb the sample to be placed therein, as known in the art.

For liquid scintillation counting, as well as for RIA and fluorescence or phosphorescence assay it may be desirable to form the bottom plate of an opaque material. The bottom plate, along with the walls, may be provided at least partially with a surface adapted to absorb the samples to be placed therein, as known in the art.

The frame cover 7 further includes supports and guide webs in the form of edge straps or pieces 9. The frame cover exterior is typically provided with opposed grip areas 10 positioned above a peripheral supporting lower rim or web 8.

Figure 2:
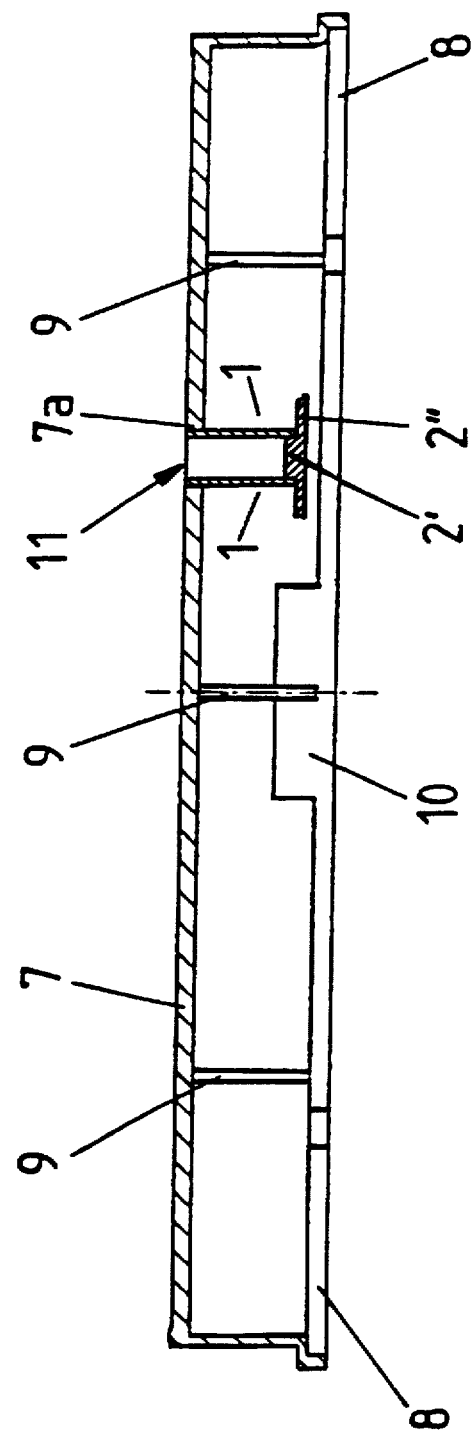
FIG. 2 presents a simplified vertical sectional view through the microtiter plate of FIG. 1 in the longitudinal axis with a representative well depicted.

As best seen in the sectional view of FIG. 2, the frame cover 7 is shown supported by its peripheral wall and surrounding supporting rim or web 8 in a manner whereby an upstanding well wall 1 is embraced in a friction fit by the hole 7a. Each of the wells 11 is aligned with a hole 7a, each well wall further surrounding and enclosing one of the plug-like elevations 2' which are arranged on the base plate 2". The walls 1 project through the frame cover 7, through the holes 7a.

Figure 3:
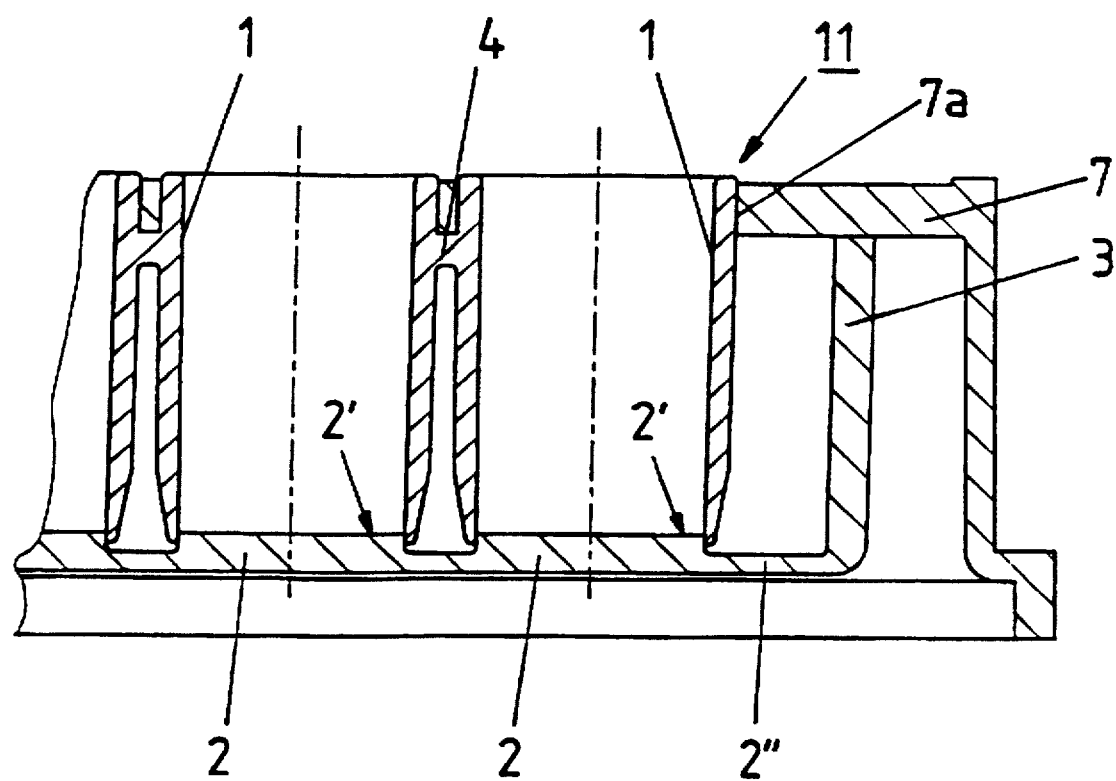
FIG. 3 is a magnified presentation of a partial sectional view through the microtiter plate of FIG. 1.
Figure 4:
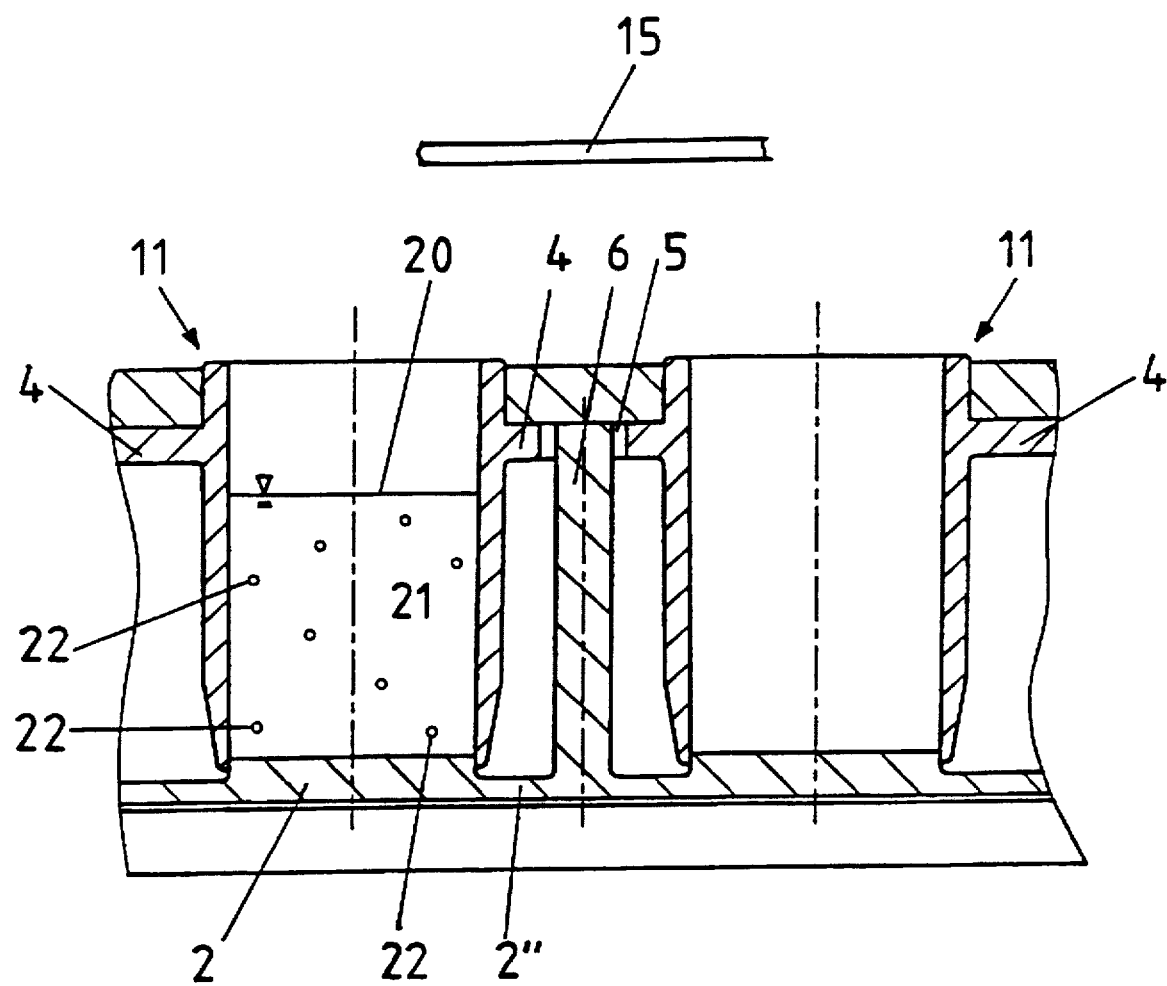
FIG. 4 is a partial sectional view through the microtiter plate of FIG. 1 further detailing the structure of the present invention.

FIGS. 3 and 4 further present the elements of the construction in greater detail. As seen therein, a connecting web 4 may be provided between the well walls 1 and allows a plurality of well walls to be formed as a unitary element. The height of the well walls 1 is chosen such that the walls are not directly touching the base (bottom) plate 2" and protrude only slightly above the frame cover 7 through its holes 7a. The plugs or elevations 2' are formed as integral raised portions upon the bottom plate 2", and define the bottoms 2 for the wells. The elevations are peripherally sealed by the well walls 1 to form the liquid-tight wells. It can be seen that the lower portion of the walls 1 receive an outside cone-shaped taper to obtain an additional desired elasticity or suppleness at such a lower end zone, permitting a snug fit about the elevations 2' to be obtained.

The bottom plate 2" is surrounded by an upturned lip or border 3 and forms a generally box-shaped peripheral supporting dish or shell, the border 3 simultaneously serving as a distance-defining element or spacer for the frame cover 7, as depicted in the right region of FIG. 3, assisting in the positioning and alignment of the cover allows the bottom plate 2" to be supported above the surface upon which the frame cover sits.

As seen in FIG. 4, a wall assembly 11 preferentially having 16 wall elements 1 joined by the connector or web 4, is guided during its mounting onto the associated elevations 2 by a series of spigot holes 5 located in the centers of the connecting pieces or webs 4 mating with the spigot shaft/distance elements 6 extending upwardly from the bottom plate 2". Upon assembly, the spigot shaft elements 6 are free in the spigot holes 5, as can be deduced from FIG. 4. By aligning the top ends of the shafts with the top surfaces of the web 4 the shafts serves to properly space the frame cover 7 from the bottom plate 2", since the frame cover is supported in a frictional fit with the tops of the well walls 1. Also depicted in FIG. 4, above the layout, is a protective cover 15 which, by the design of its border, can be configured to be mounted only in one orientation on the lay-out, as clearly depicted in FIG. 1. With a single orientation, the cover can be provided with indicia to identify the cells. Alternatively, the cell walls or the webs between the walls can be marked as desired.

Preferred construction materials are polystyrene type BASF SB 475K for the bottom plate and polypropylene type BASF PP 1324M or polypropylene type BASF PP 1325L for the walls of the wells; for the frame cover 7, polystyrene type BASF PS 144C gives satisfactory results. With use of an opaque bottom plate, the same construction material as for the frame cover 7, gives adequate results. For a wall comprising a radiation-absorbing material, a compound thermoplast, consisting for example of one of the above-mentioned polypropylenes with the addition of, for example, an appropriate amount of lead powder, as known in the art, may be employed. All parts are manufactured by commonly known pressure casting techniques. Such apolar materials allow aqueous (polar) samples, such as the liquid sample 21 containing organisms 22 as depicted in FIG. 4, to have a planar top surface 22 allowing for improved observation and analysis.

In mounting the well walls 1 it is preferred to use expanding mandrels, as known in the art, to allow the well walls to be slid over the elevations 2' without interference. This allows a tight connection to be formed without the use of glues or laborious welding techniques. The technique can be used to join a variety of so-called "unconnectable" plastics and other materials. Alternatively, heat expansion can be used during mounting.

Using materials of the type set forth above, a well layout for aqueous salt test solutions comprising 405.0 mM NaCl, 18.9 mM $MgSO_4*7H_2O$, 16.4 mM $MgCl_2*6H_2O$, 7.3 mM $CaCl_2*2H_2O$, 1.59 mM $NaHCO_3$ and 6.65 mM KCl were constructed with an overall size of 125×80 mm and a height of 15 mm. The wells were of 8.5 mm outer diameter and 7 mm inside diameter with a depth (height) of 9.5 mm.

The construction materials were evaluated for meniscus formation using a known method of video observation in the transmission mode. No meniscus was observed as being formed through 48 hours, using the above-mentioned aqueous salt solution.

It may be necessary in certain circumstances to sterilize the lay-out, and in particular the wells, using appropriate irradiation techniques. When gamma ($\delta$) irradiation is used, it is recommended that the walls be made of a material resistant to such radiation, such as BOREALIS VT 1064 KN polypropylene.

With transparent well bottoms, the invention has particular utility and value in conjunction with video observation and analysis in the transmission mode, wherein a video camera is preferably mounted below the bottoms of the wells. Shadow and contrast problems as encountered with common titerplates can be completely eliminated by the present invention.

In connection with the construction of radiation-absorbing well walls a calculation of the geometric radiation factor was undertaken. This was done utilizing the same dimension of the wells as mentioned above: 8.5 mm outer diameter, 7 mm inside diameter and a depth (height) of 9.5 mm. The distance between the two closer adjacent well centers is 9.25 mm, whereas the distance of the two neighboring wells located on the diagonal is 13.08 mm. Assuming that the radioactivity is concentrated in the center of one well, and radiates equally in all directions and forms a sphere, one can approximate the percentage of the total radiation which reaches the next well. In this approximation the changing wall thickness is not taken into account, since it is preferred to be on the safe side. For an adjacent well located the shorter distance away, the estimation results in 8.3%, for a well placed on the diagonal 3.9%. This means that at most 8.3% of the total radioactivity of β radiation would reach the neighboring well as cross talk. For α radiation one can assume that no cross talk would take place, since the radiation is not penetrating and would be absorbed by the well wall.

With an energy of 1.7 MEV, $p^{32}$ has one of the most energetic radiation of all β radiation emitting isotopes which are normally used in biological applications. Therefore, this isotope was used to measure the shielding effect of the well walls compounded with different materials. As a radiation-adsorbing material one may use a material that is crystallized in a cubic, face-centered form. It is known that the radiation-absorbing capacity of such materials show an almost linear relationship with the density of the material. Therefore, compound materials containing aluminum powder, copper powder and lead powder were used to test the efficacy in radiation protection against a $p^{32}$-source. Results obtained with an epoxide duroplast compounded with such radiation-absorbing materials are as follows:

An unshielded source showed 1750 counts per second (cps). When the source was shielded with one layer of 0.75 mm thick duroplast (corresponding to the well wall thickness) containing 30 volume percent of aluminum powder, the measurable activity dropped to 460 cps. With two layers of the same material only 250 cps could be measured. This corresponds to shielding factors of 3.8 and 7, respectively, for a single and double layer. When 30 volume percent copper powder was mixed into the same duroplast, readings of 165 cps for the single layer and 35 cps for the double layer were obtained. These give shielding factors of 11 and 50, respectively. Results obtained with different volume percentage of lead powder added to the same duroplast are summarized below:

| Volume % Pb | cps with 1 layer | cps with 2 layers | shielding factor of 1 layer | shielding factor of 2 layers |
| --- | --- | --- | --- | --- |
| 10 | 180 | 45 | 9.5 | 39 |
| 15 | 105 | 20 | 17 | 87 |
| 20 | 75 | 9 | 23 | 190 |
| 25 | 50 | 7 | 35 | 250 |
| 30 | 43 | 3 | 40 | 580 |

These results clearly indicate that one can obtain a significant shield effect by using a compound plastic for the cell wall. Since the powder is completely surrounded by the plastic the surface characteristics are the same as the original material.

With transparent well bottoms and the appropriate shielding of the well walls, the invention has particular utility and value in conjunction with video observation and analysis in the transmission mode, wherein a video camera is preferably mounted below the bottoms of the wells. Such an assembly can be used for radio-toxicity assays with little or no interference from the neighboring wells. Shadow and contrast problems as encountered with common titerplates can be completely eliminated by the present invention.

With opaque well bottoms and the appropriate shielding of the well walls, the invention has preferred utility and value in liquid scintillation counting and RIA analysis, when the detector is placed above the plates. Such an assembly, with the appropriate shielding well walls, can be used for measuring radioactivity with little or no interference from the neighboring wells.

Figure 5:
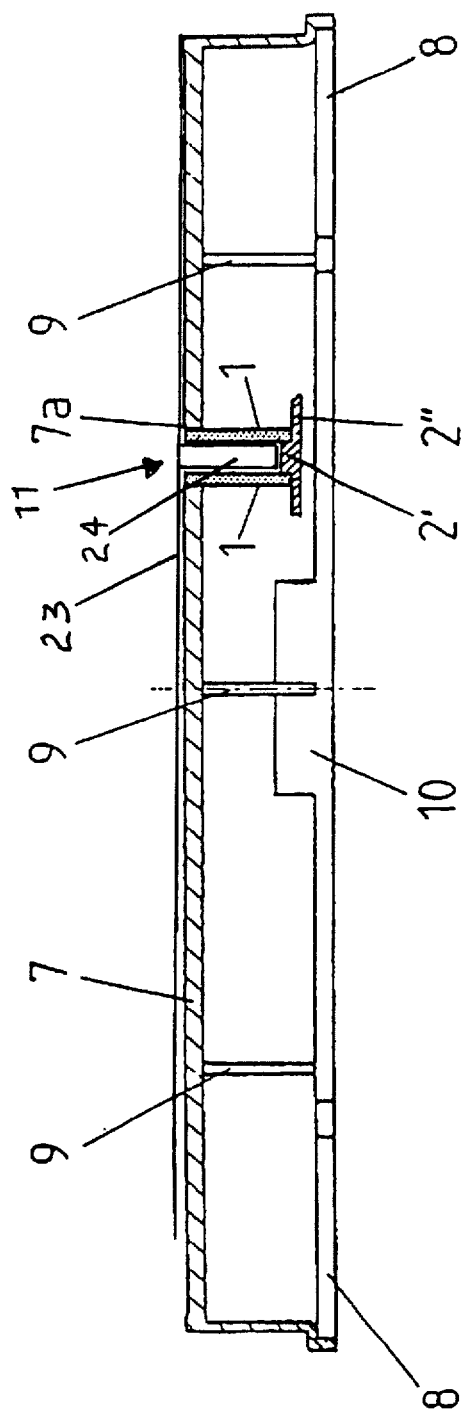
FIG. 5 is a sectional view similar to that of FIG. 2 presenting an alternative embodiment of the invention utilizing a replaceable film cover for the titerplate.

In another embodiment of the present invention, an insert is provided for use of the microtiter plate with the radiation-absorbing well walls for liquid scintillation counting of radioactive samples. The insert may be constructed of an appropriate, vacuum formed thermoplast-foil, comprising a sheet with indentations or cavities at the position of the wells, thus forming a cover or "overgarment" for the microtiter plate. This is depicted in FIG. 5. As shown therein, the foil overgarment 23 sits upon the top surface of the plate, with its formed wells or cavities 24 aligning with and overlying corresponding wells of the plate. The wells of the plate may be made incrementally larger to accommodate the indentations of the overgarment without compromising the effective volume of the wells. The radioactive samples are inserted into the formed cavities of the protective foil. After the analysis, the radioactive liquid can be withdrawn and the overgarment forming foil discarded. The plate, if not contaminated, can be reused with a new protective overgarment.

Such an overgarment is preferably made of a thermoplast which can be vacuum formed, such as polyolefine, polyvinyl chloride, polystyrene, polymethylmethacrylate, polyamide, polyacetate, polyalkylentherephtalate, polycarbonate, polyphenyleneoxide, polysulfone, polyphenylsulfide, polyimide, polyaryletherketone, fluorinated polymers, thermoplastic elastomeres, or liquid crystal polymers.

We claim:

1. A multi-well titerplate assembly for use in conjunction with instrumental analysis of liquid samples, comprising a plurality of individual wells each having a side wall and a bottom, said bottoms being arrayed whereby said bottoms are aligned in a common plane, a plurality of said bottoms being formed as a series of elevations upon a bottom plate said walls being mounted with a friction fit about the periphery of the well bottom of the well and constructed of a compound thermoplast containing a radiation-absorbing material chosen to interact with a liquid sample to be placed within the well whereby the resulting interfacial tension between the sample to be placed and the well wall results in a generally planar sample surface, the material for the well bottom being a thermoplastic material chosen to allow observation and/or analysis of the sample therethrough.

2. The assembly of claim 1, wherein the well walls are constructed of a compound thermoplast chosen from the group consisting of polyolefine, polytetrafluoroethylene, polystyrene, polystyrene co-polymer, polymethylmethacrylate, polycarbonate, polyethersulfone, polysulfone, polymethylpentene, styreneacrylnitrile, amorphous polyamid and polyethylenetherephtalate, said compound thermoplast containing a radiation-absorbing material having cubic, face-centered crystalline structures with a density above 1.5, and the well bottoms are constructed of a material chosen from the group consisting of polystyrene, polystyrene copolymer, polymethylmethacrylate, polycarbonate, polyethersulfone, polysulfone, polymethylpentene, styreneacrylnitrile, amorphous polyamid, polyethylenetherephtalate, polyolefine and polytetrafluorethylene.

3. The apparatus according to claim 1, wherein at least one of the wall and bottom of a well comprise a sample-adsorbing surface.

4. The apparatus according to claim 1, wherein at least two of said well walls are mechanically connected to form an individual sub-assembly unit.

5. The assembly according to claim 1, wherein said well walls are constructed of an apolar thermoplast and said well bottoms are constructed of a transparent thermoplastic material.

6. The assembly of claim 2, wherein the well wall material is chosen from the group consisting of polyolefine or polytetrafluoroethylene and the well bottoms are constructed of a material chosen from the group consisting of polystyrene, polystyrene co-polymer, polymethylmethacrylate, polycarbonate, polyethersulfone, polysulfone, polymethylpentene, styreneacrylnitrile, amorphous polyamid and polyethylenetherephtalate.

7. The apparatus of claim 1 furthers comprising means associated with each of the wells to identify each well and samples placed therein.

8. The apparatus according to claim 7, wherein said means comprise a common protective cover.

9. The apparatus of claim 1 further comprising a overgarment adapted and dimensioned to rest upon a top surface of said assembly and having a plurality of sample-accepting depressions aligned with a corresponding plurality of said individual wells.

10. The apparatus of claim 9, wherein said overgarment is constructed of a vacuum-formed thermoplast.

11. The apparatus of claim 10, wherein said overgarment is formed from a member of the group consisting of polyolefine, polyvinyl chloride, polystyrene, polymethylacrylate, polyamide, polyacetate, polyalkylentherephtalate, polycarbonate, polyphenyleneoxide, polysulfone, polyphenylsulfide, polymide, polyaryletherketone, fluorinated polymers, thermoplastic elastomeres, or liquid crystal polymers.

12. The apparatus of claim 1, further comprising at least one alignment shaft extending vertically upward from said bottom plate, wherein said individual sub-assembly element includes at least one spigot hole for mounting upon one of said alignment shafts.

13. The apparatus of claim 12, wherein said sub-assembly unit comprises a web portion joining the well walls, said at least one spigot hole being located in said web, said web being located vertically along said well walls to vertically align said subassembly unit with respect to said elevations when an end of said alignment shaft is co-planar with a top surface of said web.

14. The apparatus of claim 13 further comprising a top plate and a peripheral depending lip, said top plate having a series of holes therein each located and dimensioned to accept a top portion of a well wall.

15. The apparatus of claim 14, wherein said top surface of said web is adapted to support said top plate.

* * * * *